United States Patent [19]

Brownell, Sr. et al.

[11] Patent Number: 4,628,783
[45] Date of Patent: Dec. 16, 1986

[54] METHOD OF MAKING A GROOVED MEDICAL TUBE

[75] Inventors: Richard G. Brownell, Sr., Greenwich; James L. Fehl, Ft. Edward, both of N.Y.

[73] Assignee: Sherwood Medical Company, St. Louis, Mo.

[21] Appl. No.: 683,532

[22] Filed: Dec. 19, 1984

[51] Int. Cl.[4] .............................................. B26G 9/00
[52] U.S. Cl. .......................................... 83/862; 83/19; 83/49; 83/54; 83/176
[58] Field of Search ............................. 83/176, 17–21, 83/54, 861–865, 875, 49

[56] References Cited

U.S. PATENT DOCUMENTS

| | | | |
|---|---|---|---|
| 2,116,083 | 5/1938 | Rush | 83/54 X |
| 2,568,566 | 9/1951 | Sokolik | 128/240 |
| 2,711,740 | 6/1955 | Pickens | 128/349 |
| 2,743,632 | 5/1956 | Ames | 83/176 X |
| 3,136,316 | 6/1964 | Beall | 128/350 |
| 3,295,527 | 1/1967 | Alley et al. | 83/176 X |
| 3,848,604 | 11/1974 | Sackner | 128/350 R |
| 3,945,385 | 3/1976 | Sackner | 128/350 R |
| 4,181,051 | 1/1980 | Dori | 83/19 |
| 4,330,497 | 5/1982 | Agdanowski | 264/150 |

Primary Examiner—James M. Meister
Attorney, Agent, or Firm—Stanley N. Garber; Andrew J. Beck; William R. O'Meara

[57] ABSTRACT

A method of making a suction catheter having grooves and suction holes in the grooves is disclosed which includes the step of clamping a tube to effect a bulge and moving a knife longitudinally of the tube to skive the outer portion of the bulge to form a groove after clamping pressures are removed. Holes are formed in the bottom walls of the grooves. Skiving apparatus is disclosed which includes a clamping device for positioning and bulging a tube adjacent one end, and a knife relatively movable longitudinally of the tube to skive the bulge.

24 Claims, 14 Drawing Figures

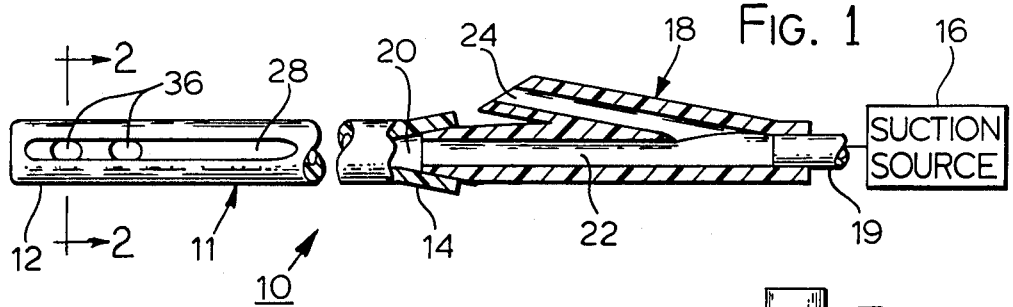
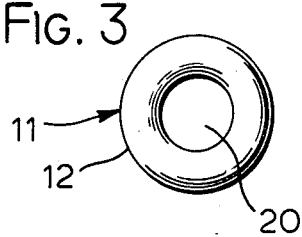
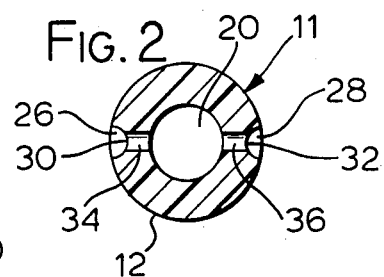
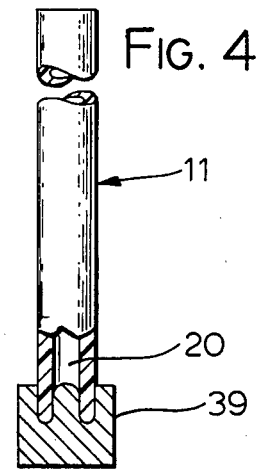
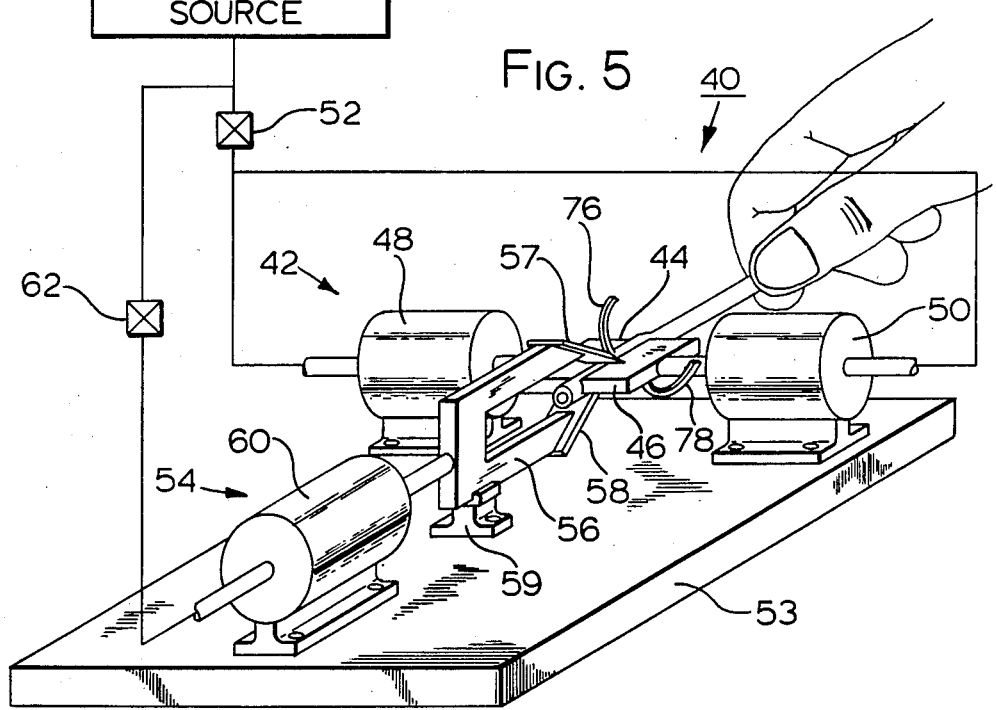

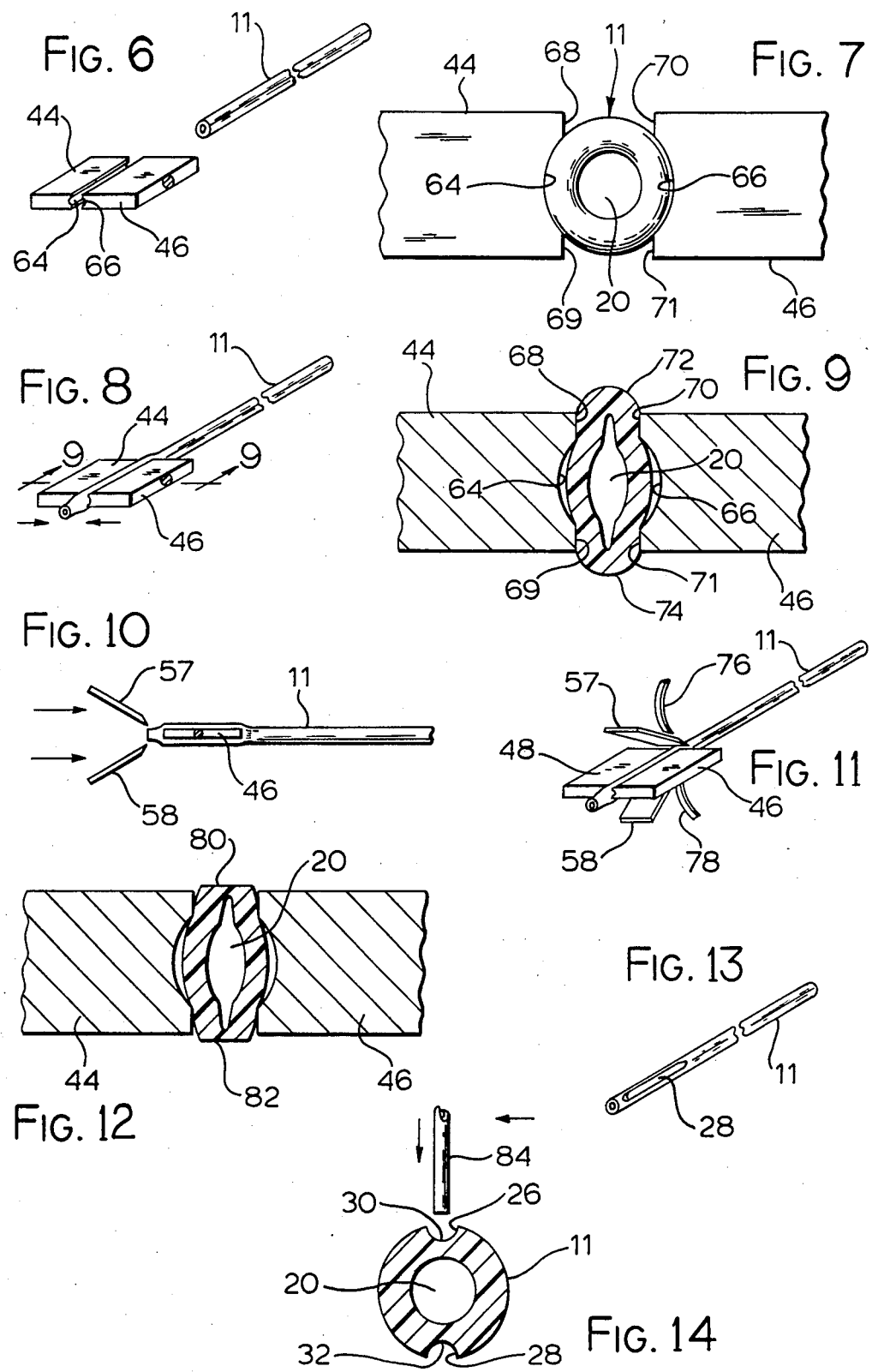

METHOD OF MAKING A GROOVED MEDICAL TUBE

DESCRIPTION

1. Technical Field

This invention relates to medical tubes and more particularly to the method of making a medical tube especially adapted for use as a suction catheter.

2. Background Art

Medical tubes, such as suction catheters, are used in a variety of applications, for example, they are used for tracheobronchial and nasopharyngeal suctioning, as well as for other suctioning applications. Such catheters may be made with an open distal end and generally with a plurality of suction openings in the sidewall of the tube adjacent the distal end.

Suction catheters have been provided with distal ends of various configurations in order to prevent or reduce invagination of the mucousa or body cavity wall tissue into the suction openings so as to prevent or reduce occulsion of the suction openings, as well as, damage and discomfort to the patient. Some thermoplastic tubes have been heated and post-formed in a die so that the distal end of the catheter has an annular radial flange. Suction openings are formed adjacent the flange so that the flange spaces the walls of the body cavity from the suction openings when the catheter is in use. However, because of the flange, the maximum usable size and fluid flow rate of the catheter for a given size body cavity or passage, is less than it would be if no flange was required.

In some cases longitudinal ridges and valleys are post-formed at the distal end of the catheter tube and suction openings are formed in the valleys so that the ridges space the openings from the body tissue. However, the valleys and ridges generally result in a catheter having a distal portion of greater outer diameter than the rest of the catheter or a portion of the lumen at the distal end of reduced size, neither of which is desirable.

U.S. Pat. No. 4,330,497 discloses a method of making a suction catheter having longitudinal grooves and suction openings in the bottom walls of the grooves and that does not require radial flanges or ridges and valleys at the distal end of the catheter. While this patent discloses a method for producing desirable catheters that avoid the above-mentioned disadvantages, it requires the coextrusion of two different plastic materials, one forming the tube and the other forming a longitudinal strip in the outer wall of the tube during extrusion. The strip must be subsquently removed to provide the grooves in the outer wall of the tube. Suction openings are then formed in the bottom walls of the grooves. These steps, however, tend to increase the cost and complexity of manufacture.

Catheter tips have been separately molded, such as by injection molding, and then bonded or adhesively connected to the end of a catheter tube. Such a construction, however, has the disadvantages of requirng the use and storage of a solvent or adhesive and the assembling step, and presents the possibility of tip separation in use.

SUMMARY OF THE INVENTION

An object of the present invention is to provide an improved method of making a medical tube having a groove formed in the outer wall of the tube and which method avoids or reduces the above-mentioned problems of prior art methods.

Another object of the present invention is to produce an effective and economical method of making a suction catheter having a groove in the outer wall of the catheter adjacent its distal end and a suction opening formed in the bottom wall of the groove and wherein precision control over the length and depth of the groove is obtained.

In accordance with one aspect of the present invention, a portion of a resilient tube is expanded by applying forces thereto, and a skiver and the tube are relatively moved to effect skiving of an outer wall portion of the expanded portion of the tube so that when the applied forces are removed, the tube has a groove in the outer wall thereof.

In accordance with another aspect of the present invention, a method of making a suction catheter is provided which include making a resilient tube in the above-described manner and then forming a suction opening in the bottom wall of the groove.

Still another aspect of the invention is to provide novel apparatus for making a groove in the outer wall of a medical tube in an especially simple, economical and accurate manner.

These, as well as other objects and advantages of the present invention, will become apparent from the following detail description and accompanying drawings.

BRIEF DESCRIPTION OF THE DRAWINGS

FIG. 1 is an elevational view of a suction catheter made in accordance with the present invention and shown connected through a vacuum control member to a schematically illustrated source of suction;

FIG. 2 is an enlarged cross-sectional view taken along line 2—2 of FIG. 1;

FIG. 3 is an enlarged left with the present invention and shown connected through a vacuum control member to a schematically illustrated source of suction;

FIG. 2 is an enlarged cross-sectional view taken along line 2—2 of FIG. 1;

FIG. 3 is an enlarged left end view of the catheter of FIG. 1;

FIG. 4 is an elevational view partly in section of a step in the method of making the catheter of FIG. 1;

FIG. 5 is a perspective view, on a reduced scale, of apparatus used in making the medical suction of FIG. 1 tube in accordance with one aspect of the present invention;

FIG. 6 is a perspective view of the clamps shown in FIG. 5 and a tube adapted to be received between the clamps in accordance with a step in the method of making the catheter of FIG. 1;

FIG. 7 is an enlarged end view showing the tube inserted between the clamps of FIG. 6;

FIG. 8 is a perspective view of the clamps and tube of FIG. 6 after the tube has been inserted between the clamps and clamping forces applied to compress the tube;

FIG. 9 is an enlarged cross-sectional view taken along line 9—9 of FIG. 8;

FIG. 10 is a right sideview of a portion of the apparatus of FIG. 5 illustrating the relative relationship between the knives, clamps, and tube during the start of the skiving operation performed by the apparatus;

FIG. 11 is a perspective view of the knives, clamps and tube during the skiving operation of the apparatus of FIG. 5;

FIG. 12 is an enlarged cross-sectional view similar to FIG. 9, but showing the tube after it has been skived;

FIG. 13 is a perspective view of the tube after the skiving step of FIG. 11 and after removal from the clamps; and FIG. 14 is cross-sectional view taken along line 14—14 of FIG. 13 along with a punch aligned with the tube grooves for forming suction holes in the tube.

DETAILED DESCRIPTION OF THE PREFERRED EMBODIMENT

Referring now to the drawings and more particularly to FIGS. 1–3, a medical tube in the form of a suction catheter is indicated generally at 10 which includes a flexible hollow shaft or tube 11. Catheter 10 has a distal end portion 12 adapted for insertion into a body cavity, such as the trachea of a patient, and a proximal end portion 14 connected to a source of suction 16 through a vacuum or suction control venting valve 18. The suction source 16 may be a conventional hospital source of suction and the valve 18 may be any suitable or conventional suction control device that can be used to vary the suction applied to the catheter 10.

Catheter tube has a lumen 20 extending throughout its length and which is open at both ends. The lumen is connected at the proximal end portion 14 with a main lumen 22 of the suction control valve 18 that, in turn, is connected in fluid communication with the suction source 16 by a tube 19. Control valve 18 has a vent port 24 that can be covered or partially convered by the thumb of the operator for allowing air from the atmosphere to enter the control valve in a controlled manner so as to control the negative pressure or suction within tube lumen 20. The port 24 can be completely occluded for maximum negative pressure or vacuum, partially opened to to effect a lower vacuum, or completely opened to further reduce or eliminate the vacuum in lumen 20.

The distal end portion 12 of tube 11 is provided with a pair of elongated, longitudinally extending grooves 26 and 28 in the outer surface or wall of tube 11 at diametrically opposite locations on the tube, as seen in FIG. 2. The bottom walls of grooves 26 and 28 are indicated at 30 and 32, respectively, and are provided with at least one suction opening or hole, two holes 34 and two holes 36, are shown respectively disposed in grooves 26 and 28 for illustration. Each of the bottom walls 30 and 32 has, of course, a radial thickness less than that of portions of the tube 11 adjacent both sides of the groove. The tube lumen 20 is not reduced in size at the distal end of the tube but rather, is of substantially constant diameter or size throughout its length thereby avoiding any fluid flow restriction. Also, the outer diameter of the tube 11 is substantially constant throughout the length of tube except at the grooves and has no radial enlargement at its distal end 12.

With this construction the distal end portion of the catheter 10 may be inserted into the trachea and controlled suction applied to the catheter so that mucous and other fluids may flow into the open distal end of lumen 20 as well as the sidewall suction openings 36 and 38. Because the openings are in the bottom walls of the grooves 26 and 28, the side walls of the grooves space the mucosa or cavity wall tissue of the patient from the sidewall openings preventing invagination of tissue into the openings and continously providng fluid flow paths from the trachea into the tube lumen 20. The suction catheter 10 may be, for example, passed through an endotracheal tube where such a tube had been previously inserted in the patient.

The present invention is particularly concerned with the method of making the catheter 10 and to the apparatus used in the method. In making catheter 10, the tube 11 may be initially formed from tubing of plastic or rubber. Tube 11 may be cut from extruded or otherwise formed plastic tubing, for example, a tubing made of a thermoplastic material which includes a polyvinyl chloride, polyurethane, polyethlene, or other suitable plastic or mixture of plastics, that may used as a catheter or other medical tube material. Elastomers such a synthetic rubber and silicone rubber may also be used. In the manufacture of suction catheters, the material may be flexible and somewhat pliable, resiliently compressible and such that the tube material can be cut either in its natural condition or in a softened condition. As used herein, "tube" is intended to mean either a discreet tube or the solidified extrudate tubing as it comes from an extruder where the tube is formed by the extrusion process.

FIG. 4 shows the tube 11 in its initial state, that is, for example, after being cut from a thermoplastic extrudate or tubing, such as from a tubular plasticized, polyvinly chloride extrudate, and after being inserted into a conventional melt or suitable heated mold 39 to smoothly round the cut or sharp edges formed by cutting the tube 11 from the plastic extrudate. The smoothly rounded end provides the distal end in the completed catheter 10 as indicated in FIGS. 1 and 3.

The method of forming each of the grooves 26 and 28 includes expanding a portion of the tube radially outwardly of the outer surface of other portions of the tube and skiving an outer section or part of the expanded tube portion. Expanding or bulging a portion of the tube, is accomplished in the preferred method by compressing or partially collapsing a predetermined portion of the tube. The skiving is preferably accomplished by relatively moving a knife and the tube, longitudinally of the tube, to cut or skive an elongate outer wall portion of the expanded or bulging portion of the tube.

FIG. 5 shows a skiving apparatus for cutting or skiving distal end portion 12 of the tube 11 to provide the grooves 26 and 28 in the finished catheter 10. Skiving apparatus 40 includes a tube clamping device 42 having a pair of similar, opposed clamping jaws or clamps 44 and 46 for receiving, holding and clamping or compressing the tube 11 to expand or bulge portions of tube 11, as will be further described hereafter. The clamps are operated between predetermined open and closed positions by a pair of actuators or motors 48 and 50, respectively, which may be conventional air, vacuum or hydraulic motors or other suitable actuators. As shown for example, the motor 48 and 50 are pressurized air actuated motors connected to a pressurized air source 51 through an air flow control valve 52. The actuators 48 and 50 are fixed to a plate or table 53 such as by bolts.

The skiving device 40 also includes a skiver or tube cutting device 54. Skiver 54 includes a knife holder 56 to which is attached a pair of knives or cutting blades 57 and 58, such as by bolts (not shown). The knife holder 54 is guided for linear movement longitudinally for the tube 11 during skiving operations by any suitable guide member, for example, a member 59 is shown for illustration as having a groove in which the holder 56 is slidable. The guide member 59 is secured to plate 53, such as bolts, so that the knife holder 56 and knives 57 and 58 are accurately guided for movement longitudinally of the tube 11 when the tube is held by clamps 44 and 46. Holder 56 is moved by an air motor or actuator 60 mounted to plate 53 and connected to move the holder. Skiver actuator 60 may be controlled by an air flow control valve 62 connected to the pressurized air source 51. Each of the actuators 48, 50, and 60 may be actuated, for example, in a forward direction by air pressurization and returned by an internal spring to the rearward or deactuated position. The valves 52 and 62 may be conventional valves of the manually controlled type or they may be automatically controlled as desired.

In utilizing the skiving apparatus 40 to form grooves 26 and 28 in the outer surface of the distal end portion 12 of the tube 11 after the distal tip of the tube has been melted molded as in FIG. 4, the tube is inserted, distal end first, between the relatively movable clamps 44 and 46 of skiving apparatus 40. The tube 11 may be inserted and the proximal end portion held by hand as shown in FIG. 5. FIG. 6 illustrates the tube 11 just prior to insertion between the jaws in the clamping device 42. Preferably, the tube 11 is inserted into the clamps until the distal end extends slightly out of the clamps as in FIG. 5. The opposed facing clamping surfaces of the clamps 44 and 46 have arcuate portions 64 and 66 respectively which form arcs substantially complementary to arcuate portions on the outer surface of tube 11. When the clamps are in the open or unactuated position, as in FIG. 6 and 7, the tube 11 can be guided into accurate position between the clamping members 44 and 46 by the facing arcuate surfaces 64 and 66. The facing surface of the clamp 44 also has a pair of longitudinally extending flat parallel surfaces 68 and 69 at the upper and lower edges of the clamp. Similarly, the facing surface of clamp 46 has a pair of longitudinally extending flat parallel surfaces 70 and 71 and which respectively face and are in lateral alignment with flat surfaces 68 and 69 of jaw 44. These flat facing surfaces of the clamps engage and move opposed sides of the tube 11 toward each other to compress and effect bulging of the tube 11 in preparation for skiving it, as will be described.

After the tube 11 is inserted into the space between the clamps 44 and 46, as in FIG. 7, so that the arcuate surfaces 64 and 66 acturately locate and hold the tube 11 in the desired position, the clamps 44 and 46 are actuated by actuators 48 and 50 (FIG. 5) so that they move relative to each other and the tube 11 to apply clamping forces to the opposed sides of the tubes as seen in FIGS., 8-10, thereby compressing the predetermined portion of the tube and causing upper and lower diametrically opposed radial protrusions or bulges 72 and 74. As best seen in FIG. 9, the facing flat surfaces 68 and 70 of the clamps move relative to each other and tube 11 such that they squeeze or compress an upper portion of tube 11 causing the bulge 72 while the facing surfaces 69 and 71 of the clamps move relative to each other and tube 11 so as to squeeze or compress the lower diametrically opposed portion of tube 11 and effect the bulge 74.

In FIG. 9, the movement of the clamps 44 and 46 relatively toward each other are limited, such as by suitable stops or the like (not shown) to provide a predetermine clamping pressure. As shown, a pressure is applied so that the tube lumen 20 does not fully close and the inner walls of the tube become generally eliptical. As shown, the lumen 20, is no longer of the same configuration and cross-section as in its original or unclamped shape, that is, the inner walls of the lumen 20 are no longer round at the clamped portion of the tube but facing walls of the tube do not contact each other although they may do so depend upon the clamping pressure applied to the tube. It is seen from FIGS. 7 and 9 that the tube 11, before being squeezed by the clamp 44 and 46 is circular in cross-section and its outer diameter is less than the vertical height of the clamps 44 and 46 and the outer wall or surface of tube 11 does not extend above or below the upper and lower surfaces of the clamps. However, after the tube is clamped or compressed, as best shown in FIG. 9, the diametrically opposed bulges 72 and 74 do extend above and below the upper and lower surfaces of the clamps.

In FIG. 10, the knives 56 and 58 are shown positioned for longitudinal movement rightwardly to effect skiving the longitudinally extending bulges 72 and 74. In FIG. 11, the knives 56 and 58 are shown effecting the skiving, that is, cutting longitudinal chips indicated at 76 and 78 from the outer wall or surfaces of the bulges 72 and 74 of the tube. The knives are moved by actuator 60 as controlled by valve 62. Tube 11 in FIG. 12 is shown clamped between the clamps 44 and 46 and after having been skived by the knives 56 and 58. It will be seen that in the clamped condition of the tube, the knives, which move longitudinally along the tube, cut off the radialy outer portions or tops of the bulges 72 and 74 so that the remaining outer surfaces of the bulges are flat. These flats, which are indicated at 80 and 82 in FIG. 12, are flat both longitudinally along the tube as well as laterally or in a direction normal to the longitudinal axis of the tube.

After skiving tube 11, the clamps 44 and 46 are returned to the normally open position, the position shown in FIGS. 6 and 7. The tube 11 may then be pulled longitudinally out of the clamps. Due to the resilency of the tube 11, the distal end portion will be returned to its original shape (naturally or mechanically assisted) so that the lumen 20 in the distal end portion of the tube will return to its original shape, in this case, the lumen walls become circular again. The tube 11 will appear as shown in FIG. 13. Because the tube was squeezed or clamped to effect bulging as in FIG. 9, that flat areas or portions 80 and 82 after skiving as shown in FIG. 12, become the curved or generally arcuate grooves 26 or 28, as best seen in FIGS. 2 and 14, when the clamping pressures are removed from the tube as when it is removed from the clamps of clamping device 42.

After the tube 11 is provided with grooves 26 and 28, the suction openings or holes 34 and 36 (FIG. 2) are formed. This may be accomplished by aligning a hollow punch, such as indicated at 84, with the grooves 26 and 28, as seen in FIG. 14 and then moving the punch 84 through both of the bottom walls 30 and 32, such as during a single stroke of the punch, to produce the holes 34 and 36. Where desired, other methods of forming the suction openings may be used, for example, a mandrel may be inserted into the tube lumen 20 and individual punches used to punch the suction openings.

The tube clamping device 42 of skiving apparatus 40 performs the functions of receiving and holding a tube accurately in the desired location for processing since the outer surfaces of the clamps 44 and 46 conform to the engaging outer portion of the tube (FIG. 7). While the surfaces are arcs of circles when the tube is circular in section, the facing surfaces of the clamps may be shaped differently where the outer surface of the tube is normally noncircular, such as eliptical or the like. The clamps of the clamping device 42 not only squeeze or collapse the walls of the tube to effect the described bulging of the tube for skiving or cutting the grooves in the outer surface or wall of the bulges but also serve to accurately locate and hold the tube during skiving to obtain accurately controlled grooves. While the facing surfaces of the clamps are shown complementary to the surfaces of the tube, it is not necessary for the facing surfaces of the clamps to be complementary to the tube or to each other in order that the clamps locate and position to tube for skiving.

Preferably, the cutting edge of each knife is straight and extends normal to the longitudinal axis of the tube (FIGS. 5, 10 and 11). The knives 56 and 58 of device 42 are positioned so that when moving longitudinally along the tube to effect skiving, they do not engage the clamps 44 and 46. since the tube is bulged by clamping forces and such that the bulge extends radially outward beyond the normal outer surface of the tube, and the knives 56 and 58 move only longitudinally, the tube is cut only where the bulge occurs. Thus skiving apparatus many be made simply and economically and yet produce accurately controlled and located groovess. Catheters made by the above described method and apparatus are effective and atraumatic.

Where desired, one of the clamps, such as clamp 44 may be made stationery so that only one clamp is movable to thereby eliminate the need for one of the actuators 48 and 50. Also, while two grooves 26 and 28 are advantageously similtaneously formed in diametrically opposite sides of the tube by apparatus 40, a single knife could be used to skive one groove at a time if desired. Also, a suction tube could be provided with one or more than two grooves as desired.

As various changes could be made in the above described methods and apparatus without departing from the scope of the invention it is intended that all matter contained in the above description or shown in the drawings shall be interpreted as illustrative and not in a limiting sense.

What is claimed is:

1. A method of making a resilient flexible medical tube having a groove in the exterior surface of the wall of the tube and an opening through the bottom wall of the groove connecting the grove with the lumen of the tube comprising the steps of applying predetermined forces to a resilient flexible tube to expand a portion of the wall of the tube, skiving the expanded wall portion to remove an outer part of the wall thereof, removing the applied forces to thereby allow the expanded wall portion to return to its unexpanded condition and effect a groove having spaced opposed sidewalls and a bottom wall in the exterior surface of the wall of the tube where the outer part of the wall was removed, and forming a opening extending through that portion of the wall of the tube that forms the bottom wall of the groove to connect the groove with the lumen of the tube.

2. The method of claim 1 wherein said step of applying forces includes positioning the tube between a pair of clamping members, and moving at least one of the clamping members toward the other to compress a predetermined portion of the tube therebetween and effect at least a partial collapse of the tube lumen and a bulge with the expanded portion of the wall thereon.

3. The method of claim 2 wherein said skiving step includes effecting relative movement between a knife and the tube so that the knife cuts the radially outer part of the wall of the expanded portion and whereby the groove has a bottom wall of less thickness than portions of the sidewall of the tube adjacent the groove.

4. A method of forming a groove in the exterior surface of the wall of a resilient flexible medical tube comprising the steps of applying predetermined forces to a resilient flexible tube to expand a portion of the wall of the tube, skiving the expanded wall portion to remove an outer part of the wall thereof, removing the applied forces to thereby allow the expanded wall portion to return to its unexpanded condition and effect a groove having spaced opposed sidewalls and a bottom wall in the exterior surface of the wall of the tube where the outer part of the wall was removed, said step of applying forces including positioning the tube between a pair of clamping members, and moving at least one of the clamping members toward the other to compress a predetermined portion of the tube therebetween and effect at least a partial collapse of the tube lumen and a bulge with the expanded portion of the wall thereon, said skiving step including effecting relative movement between a knife and the tube so that the knife cuts the radially outer part of the wall of the expanded portion and whereby the groove has a bottom wall of less thickness than portions of the sidewall of the tube adjacent the groove, and forming an opening extending through the bottom wall of the groove subsequent to removing said applied forces.

5. A method of forming a groove in the exterior surface of the wall of a resilient flexible medical tube comprising the steps of applying predetermined forces to a resilient flexible tube to expand a portion of the wall of the tube, skiving the expanded wall portion to remove an outer part of the wall thereof, and removing the applied forces to thereby allow the expanded wall portion to return to its unexpanded condition and effect a groove having spaced opposed sidewalls and a bottom wall in the exterior surface of the wall of the tube where the outer part of the wall removed, said step of applying forces including positioning the tube between a pair of clamping members, and moving at least one of the clamping members toward the other to compress a predetermined portion of the tube therebetween and effect at least a partial collapse if the tube lumen and a bulge with the expanded portion of the wall thereon, said skiving step including effecting relative movement between a knife and the tube so that the knife cuts the radially outer part of the wall of the expanded portion and whereby the groove has a bottom wall of less thickness than portions of the sidewall of the tube adjacent the groove, the expanded portion extending radially outwardly of the outer surface of the clamping members, said skiving step including moving a cutting blade longitudinally of the tube and in a plane spaced from the clamping member to cut the radially outer part of the wall of the expanded portion from the tube, said step of removing the forces from the tube including moving at least one of the clamping members to free the tube.

6. A method of forming a groove in the exterior surface of the wall of a resilient flexible medical tube comprising the steps of applying predetermined forces to a resilient flexible tube to expand a portion of the wall of the tube, skiving the expanded wall portion to remove an outer part of the wall thereof, and removing the applied forces to thereby allow the expanded wall portion to return to its unexpanded condition and effect a groove having spaced opposed sidewalls and a bottom wall in the exterior surface of the wall of the tube where the outer part of the wall was removed, said step of applying forces including positioning the tube between a pair of clamping members, and moving at least one of the clamping members toward the other to compress a predetermined portion of the tube therebetween an effect at least a partial collapse of the tube lumen and a bulge with the expanded portion of the wall thereon, said skiving step including effecting relative movement between a knife and the tube so that the knife cuts the radially outer part of the wall of the expanded portion and whereby the groove has a bottom wall of less thickness than portions of the sidewall of the tube adjacent the groove, of the clamping members having facing surface configurations such that the tube is predeterminately located thereby between the clamping members prior to the step of applying the compressive forces to the tube.

7. The method of claim 6 wherein at least one clamping members has a facing surface configuration that is arcuate and the tube has an arcuate outer surfaces portion which fits within the arcuate surface of the one clamping member to predeterminately locate the tube relative to the clamping members and the knife.

8. A method of forming a groove in the exterior surface of the wall of a resilient flexible medical tube comprising the steps of applying predetermined forces to a resilient flexible tube to expand a portion of the wall of the tube, skiving the expanded wall portion to remove an outer part of the wall thereof, and removing the applied forces to thereby allow the expanded wall portion to return to its unexpanded condition and effect a groove having a spaced opposed sidewalls and a bottom wall in the exterior surface of the wall of the tube where the outer part of the wall was removed, said step of applying forces to the tube including squeezing a predetermined portion of the tube between a pair of clamping members to effect a pair of expanded portions at the oppositesides of the tube and which bulge radially outwardly beyond the opposed outer surfaces of portions of the tube which are not squeezed, said skiving step including moving a pair of cutting blades longitudinally of the tube to remove a radially outer portion of the wall of each of the expanded portions to form said groove and a groove on the opposed side of the tube when the applied forces are removed.

9. The method of claim 1 wherein the lumen of the tube is a least partially collapsible, and the tube is of flexible and resilient material which substantially returns to its normal configuration after said forces have been removed therefrom, and said groove extends longitudinally of said tube.

10. The method of claim 1 wherein the tube is formed from extruded thermoplastic material.

11. The method of claim 1 wherein the tube is formed of an elastomeric material.

12. The method of claim 1 wherein said step of skiving includes cutting the expanded portion to form an elongate substantially flat surface while the predetermined forces are applied to form a substantially arcuate groove when the predetermined forces are removed.

13. The method of claim 12 wherein the tube in normally substantially circular in cross-section.

14. The method of claim 1 wherein said tube has a lumen which extends through said expanded wall portion.

15. The method of making a suction catheter comprising the steps of providing a resilient flexible tube, positioning the tube between a pair of relatively moveable clamping members, effecting relative movement between at least one member and the tube to squeeze a predetermined longitudinally extending portion of the tube between the members so as to form a bulge on the tube which extend outwardly beyond the outer surface of the portions of the tube which are not squeezed, effecting relative movement between a knife and the tube so that the knife skives the outer surface of the wall of the bulge to effect an elongate groove in the outer wall of the tube having spaced opposed sidewalls and a bottom wall when the tube is released from the members, effecting relative movement of the members so as to release the tube therefrom, and forming at least one opening through the wall of the tube such that the groove connects with the opening and the lumen of the tube.

16. The method of claim 15 wherein the skiver effects a substantially flat elongate area on the bulge.

17. The method claim 16 wherein the tube has substantially constant inner and outer diameters throughout its length and is at least partially collapsed to form the bulge.

18. The method of claim 15 wherein the step of squeezing the predetermined portion of the tube includes effecting a second bulge on the side opposite the side on which first named bulge is effected, and skiving the second bulge to effect a second elongate groove in the outer wall of the tube when the tube is released from the clamping members, and forming at least one opening through the bottom wall of the second groove which connects with the lumen of the tube.

19. The method of claim 18 wherein a second knife is provided, and the second knife is moved with the first named knife to effect simultaneous skiving of the bluges.

20. The method of claim 19 wherein the knives have cutting edges extending substantially normal and parallel to the longitudinal axis of the tube and are moved in a longitudinal direction relative to the tube so that skiving cuts and removes outer parts of both bulges and effects substantially flat elongate outer surface areas while the predetermined portion of the tube is squeezed, and removing the tube from between the clamping members so that the flat surface areas become elongate grooves in the outer wall of the tube.

21. Apparatus for producing a resilient suction catheter having a suction opening in the sidewall of the catheter tube which has walls on opposed sides thereof to prevent invagination of tissue into the opening comprising a pair of clamping members, control means for moving said clamping members relatively toward and away from each other, said clamping members having spaced facing surfaces for receiving a resilient tube which is at least partially collapsible, said clamping members being relatively movable toward each other to at least partially collapse the tube when placed therebetween so that a portion of the tube bulges radially outwardly of portions of the tube not partially collapsed, tube cutting means including a cutting element for skiving material of the tube, means for effecting relative movement between the cutting element and the tube for moving said element relativelly longitudinally of the tube in the plane parallel to the longitudinal axis of the tube to skive a longitudinal radially outer wall portion only from the bluge to form a flat longitudinally extending area, said clamping members being movable relatively away from each other to allow the flat area of the tube to form a groove having sidewalls and a bottom wall, and means for forming an opening through the bottom wall of the formed groove, said clamping members having facing surfaces engageable with opposed sides of the tube to at least partially collapse the tube and effect a second bulge on the partially collapsed tube at a location diametrically opposite the first named bulge and which extends radially outwardly beyond the radially outer surface of tube not partially collapsed, said tube cutting means including a second cutting element, and said means for moving said element including means for moving said second cutting element longitudinally of the tube to skive a radially outer longitudinally extending wall portion of the second bulge.

22. Apparatus for producing a resilient suction catheter having a suction opening in the sidewall of the catheter tube which has walls on opposed sides thereof to prevent invagination of tissue into the opening comprising a pair of clamping members, control means for moving said clamping members relatively toward and away from each other, said clamping members having spaced facing surfaces for receiving a resilient tube which is at least partially collapsible, said clamping members being relatively movable toward each other to at least partially collapse the tube when placed therebetween so that a portion of the tube bulges radially outwardly of portions of the tube not partially collapsed, tube cutting means including a cutting element for skiving material of the tube, means for effecting relative movement between the cutting element and the tube for moving said element relatively longitudinally of the tube in a plane parallel to the longitudinal axis of the tube to skive a longitudinal radially outer wall portion only from the bluge to form a flat longitudinally extending area, said clamping members being movable relatively away from each other to allow the flat area of the tube to form a groove having sidewalls and a bottom wall, and means for forming an opening through the bottom wall of the formed groove, said cutting elements being movable simultaneous longitudinally of a tube to be skived and spaced from each other to cut only the bulges of the tube.

23. A method of forming a groove in the exterior surface of the wall of a resilient flexible medical tube comprising the steps of applying predetermined forces to a resilient flexible tube to expand a portion of the wall of the tube, skiving the expanded wall portion to remove an outer part of the wall thereof, removing the applied forces to thereby allow the expanded wall portion to return to its unexpanded condition and effect a groove having spaced opposed sidewalls and a bottom wall in the exterior surface of the wall of the tube where the outer part of the wall was removed, said step of applying forces including positioning the portion of the tube between a pair of clamping members, and moving at least one of the clamping members toward the other to compress a predetermined portion of the tube therebetween and effect at least a partial collapse of the tube lumen and a bulge with the expanded portion of the wall thereon, said skiving step including effecting relative movement between a knife and the tube so that the knife cuts the radially outer part of the wall of the expanded portion and whereby the groove has a bottom wall of less thickness than portions of the sidewall of the tube adjacent the groove, the knife cutting the outer part of the wall of the expanded portion to form an elongated section which is substantially flat in both lateral and longitudinal directions.

24. The method of making a suction catheter comprising the steps of providing a resilient flexible tube, positioning the tube between a pair of relatively moveable clamping members, effecting relative movement between at least one member and the tube to squeeze a predetermined longitudinally extending portion of the tube between the members so as to form a bulge on the tube which extend outwardly beyond the outer surface ot the portions of the tube which are not squeezed, effecting relative movement between a knife and the tube so that the knife skives the outer surface of the wall of the bluge to effect an elongate groove in the outer wall of the tube having spaced opposed sidewalls and a bottom wall when the tube is released from the members, effecting relative movement of the members so as to release the tube therefrom, and forming at least one opening through the wall of the tube such that the groove connects with the opening and the lumen of the tube, the step of forming at least one opening including forming an opening after the skiving step and after the tube has been released from the clamping members.

* * * * *